United States Patent

Hou et al.

[11] Patent Number: 6,103,122
[45] Date of Patent: Aug. 15, 2000

[54] FILTER SHEET FOR PURIFYING PHOTORESIST COMPOSITION

[75] Inventors: Kenneth C. Hou, Monroe; Eugene A. Ostreicher, Farmington; Richard D. Sale, Tolland, all of Conn.

[73] Assignee: Cuno Incorporated, Meriden, Conn.

[21] Appl. No.: 08/903,101

[22] Filed: Jul. 30, 1997

Related U.S. Application Data

[60] Provisional application No. 60/022,793, Jul. 30, 1996.

[51] Int. Cl.[7] .................................................. B01D 39/18
[52] U.S. Cl. .................................. 210/502.1; 162/164.2; 162/181.1; 162/181.6; 162/181.8; 210/504; 210/505; 210/508
[58] Field of Search .............................. 210/502.1, 503, 210/504, 505, 506, 508; 162/164.2, 181.6, 181.1, 181.8

[56] References Cited

U.S. PATENT DOCUMENTS

| | | | |
|---|---|---|---|
| 3,327,859 | 6/1967 | Pall | 210/282 |
| 3,420,709 | 1/1969 | Barrett et al. | 210/503 |
| 4,007,113 | 2/1977 | Ostreicher | 210/504 |
| 4,007,114 | 2/1977 | Ostreicher | 210/505 |
| 4,193,876 | 3/1980 | Leeke et al. | 210/489 |
| 4,288,462 | 9/1981 | Hou et al. | 210/777 |
| 4,305,782 | 12/1981 | Ostreicher et al. | 210/503 |
| 4,309,247 | 1/1982 | Hou et al. | 210/505 |
| 4,321,288 | 3/1982 | Ostreicher | 210/505 |
| 4,347,208 | 8/1982 | Southall | 264/229 |
| 4,361,486 | 11/1982 | Hou et al. | 210/505 |
| 4,366,068 | 12/1982 | Ostreicher et al. | 210/767 |
| 4,488,969 | 12/1984 | Hou | 210/679 |
| 4,511,473 | 4/1985 | Hou | 210/502.1 |
| 4,578,150 | 3/1986 | Hou | 210/505 |
| 4,596,660 | 6/1986 | Hou | 210/692 |
| 4,606,824 | 8/1986 | Chu et al. | 210/635 |
| 4,617,128 | 10/1986 | Ostreicher | 210/679 |
| 4,645,567 | 2/1987 | Hou et al. | 210/777 |
| 4,783,262 | 11/1988 | Ostreicher et al. | 210/314 |
| 4,859,340 | 8/1989 | Hou et al. | 210/502.1 |
| 4,881,313 | 11/1989 | Artinyan | 29/163.8 |
| 4,915,839 | 4/1990 | Marinaccio et al. | 210/500.23 |
| 5,045,210 | 9/1991 | Chen et al. | 210/679 |
| 5,055,192 | 10/1991 | Artinyan et al. | 210/346 |
| 5,085,780 | 2/1992 | Ostreicher | 210/683 |
| 5,085,784 | 2/1992 | Ostreicher | 210/767 |
| 5,192,446 | 3/1993 | Salem et al. | 210/685 |
| 5,284,930 | 2/1994 | Matsumoto et al. | 528/482 |
| 5,288,850 | 2/1994 | Matsumoto et al. | 528/482 |
| 5,346,624 | 9/1994 | Libutti et al. | 210/679 |
| 5,350,714 | 9/1994 | Trefonas, III et al. | 210/660 |
| 5,376,278 | 12/1994 | Salem | 210/679 |
| 5,378,802 | 1/1995 | Honda | 528/480 |
| 5,446,125 | 8/1995 | Honda et al. | 528/486 |
| 5,500,127 | 3/1996 | Carey et al. | 210/685 |
| 5,521,052 | 5/1996 | Rahman et a. | 210/660 |
| 5,525,315 | 6/1996 | Burke | 423/24 |
| 5,578,245 | 11/1996 | Ziolo | 252/314 |
| 5,595,649 | 1/1997 | Markell et al. | 210/502.1 |

OTHER PUBLICATIONS

MicroLite "Recommended Usage Table", p. 7090 Apr. 1990.
MicroLite "PrCN Cation–Ammonia Form", p. 7040 Apr. 1990.
CUNO "Zeta Plus EC Series Filter Systems for Trace Metals Removal" brochure.
Graver Chemical Company Profile.

*Primary Examiner*—Ivars Cintins
*Attorney, Agent, or Firm*—Steven J. Moore; Cummings & Lockwood

[57] ABSTRACT

A filter sheet is provided which comprises a self-supporting fibrous matrix having immobilized therein particulate filter aid and particulate ion exchange resin, wherein said particulate filter aid and particulate ion exchange resin are distributed substantially uniformly throughout a cross-section of said matrix. A process for removing ionic impurities from a photoresist solution is also provided which comprises passing the photoresist solution through said filter sheet to remove ionic impurities therefrom.

35 Claims, 2 Drawing Sheets

Effect of IEX Particle Size on Performance

FILTER SHEET FOR PURIFYING PHOTORESIST COMPOSITION

This application claims the benefit of U.S. Provisional Application No. 60/022,793, filed Jul. 30, 1996.

FIELD OF THE INVENTION

This invention relates to a filter sheet and process for purifying a photoresist composition employing said filter sheet and, more particularly, to the removal of ionic contaminants from photoresist compositions utilizing said filter sheet, said filter sheet comprising a self-supporting fibrous matrix having immobilized therein particulate filter aid and particulate ion exchange resin.

BACKGROUND OF THE INVENTION

Photoresist compositions are used extensively in integrated circuit manufacture. Such compositions typically comprise a light-sensitive component and a polymer binder dissolved in a polar organic solvent. Typical photoresist compositions are disclosed in U.S. Pat. Nos. 5,178,986, 5,212,046, 5,216,111 and 5,238,776, each incorporated herein by reference for disclosure of photoresist compositions, processing and use. Impurity levels in photoresist compositions are becoming an increasingly important concern. Impurity contamination, especially by metals, of photoresists may cause deterioration of the semiconductor devices made with said photoresists, thus shortening these devices' lives. Impurity levels in photoresist compositions have been and are currently controlled by (1) choosing materials for photoresist compositions which meet strict impurity level specifications and (2) carefully controlling the photoresist formulation and processing parameters to avoid the introduction of impurities into the photoresist composition. As photoresist applications become more advanced, tighter impurity specifications must be made.

Efforts to remove dissolved ionic contaminants from organic liquids, such as photoresist compositions, are known in the art. For example, U.S. Pat. No. 5,045,210 discloses an ion exchange media containing a modified polysaccharide material and a modified silica or modified particulate polymeric material, said modified materials including a polysaccharide and silica or particulate polymer material covalently bonded to a synthetic polymer having chemical groups capable of coupling to the polysaccharide, silica and/or particulate polymer.

U.S. Pat. Nos. 5,284,930 and 5,288,850 disclose processes for removing metals from photoresist vinyl phenol polymer solutions which entail passing the solutions through an ion-exchange column comprising a strongly acidic cation exchange resin.

U.S. Pat. No. 5,346,624 describes a method for removing ionic and suspended particulate impurities from a liquid by passing the liquid through a bed comprising a mixture of powdered ion exchange resin particles, ion exchange fibers and relatively inert fibers.

U.S. Pat. No. 5,350,714 describes a process whereby organic solutions are treated to remove contaminants immediately prior to use of the solution ("point-of-use purification"). The process involves the use of contaminant removal means at the point of end use of the solution, the contaminant removal means containing a bed comprising ion exchange resin, activated carbon or mixtures thereof.

U.S. Pat. No. 5,376,278 discloses a method of removing charged particles from a liquid stream by passing the liquid stream through a filter sheet which is conditioned by pre-coating an ion exchange material on the surface of the filter sheet.

U.S. Pat. No. 5,378,802 discloses a method of removing ionic impurities from a photoresist which involves dissolving the photoresist in a solvent, contacting the resulting photoresist composition resist component with a fibrous ion exchange resin and separating the ion exchange resin bearing the metal impurities from the photoresist composition.

U.S. Pat. No. 5,500,127 describes a process for purifying an acid catalyzed photoresist which comprises passing the photoresist through a column containing a weak acid cation exchange resin and a strong base anion exchange resin.

U.S. Pat. No. 5,521,052 discloses a process for producing novolak resins containing low levels of metal ions. The process entails passing novolak resin through an anion exchange resin which has been treated with deionized water and mineral acid followed by passing the solution through a cation exchange resin which has been treated with deionized water and mineral acid.

U.S. Pat. No. 5,525,315 discloses a process for removing dissolved heavy metal ions from an organic solution which involves passing the organic solution through a bed containing cation exchange resin having chelating groups on the resin or slurrying the organic solution with a solution containing the chelating exchange resin.

Filter media previously employed in the filtration of photoresists are known which comprise a self-supporting matrix of celluose fibers having immobilized therein particulate filter aid and binder resin. Such filter media are sold under the tradename Zeta Plus® EC Series (CUNO, Inc., Meriden, Conn., U.S.A.) and do not contain ion exchange resin embedded therein.

SUMMARY OF THE INVENTION

In accordance with the present invention, a filter sheet is provided which comprises a self-supporting fibrous matrix having immobilized therein particulate filter aid and particulate ion exchange resin, wherein said particulate filter aid and particulate ion exchange resin are distributed substantially uniformly throughout a cross-section of said matrix. It has been surprisingly discovered that the filter sheet of this invention exhibits a significantly higher ion exchange capacity compared to the ion exchange capacity of the ion exchange resin alone, notwithstanding the fact that the other major constituents of the subject filter sheet, namely, the fibers utilized to form the fibrous matrix and the particulate filter aid, possess little or no ion exchange capacity themselves. Further in accordance with the present invention, a process for removing ionic impurities, e.g., metal cations, from an organic liquid, e.g., a photoresist solution, is provided which comprises passing the ionic impurity-containing organic liquid through the filter sheet to provide a purified photoresist composition. The process of this invention results in the reduction of ionic impurities down to low parts per billion levels in photoresist compositions.

DESCRIPTION OF THE PREFERRED EMBODIMENTS

The filter sheet of this invention is comprised of an amount of particulate filter aid and particulate ion exchange resin immobilized in a substantially inert porous matrix. The filter sheet of this invention contains extremely small amounts, i.e., very low parts per billion (ppb) levels, of extractable metal impurities which can be introduced into filtrates such as photoresist compositions. As a result, the filter sheet of the invention is particularly useful in the purification of photoresist compositions.

The porous matrix may be any matrix material capable of immobilizing the particulate filter aid and particulate ion exchange resin contained therein, i.e. one capable of preventing loss of particulate filter aid and particulate ion exchange resin from the filter sheet. The filter sheet possesses a porosity which enables the fluid being filtered to pass through the filter while entrapping or retaining captured particulate contaminants and dissolved ionic contaminants. In order to provide a matrix which is a coherent and a handleable structure, it is desirable that at least one of the components which go into forming the porous matrix be a long, self-bonding structural fiber. Such fiber gives the filter sheet sufficient structural integrity in both the wet "as formed" condition and in the final dried condition. Such a structure permits handling of the filter media during processing and at the time of its intended use. Suitable fibers which may be utilized in the present invention include polyacrylonitrile fibers, nylon fibers, rayon fibers, polyvinyl chloride fibers, cellulose fibers, such as wood pulp and cotton, and cellulose acetate fibers.

The preferred filter sheet of this invention possesses a porous matrix comprised of a self-bonding matrix of cellulose fibers. Such fibers can represent from about 15 to about 80 weight percent, preferably from about 40 to about 70 weight percent, of the filter sheet of this invention. Where cellulose fibers are employed in the fabrication of the filter sheet of this invention, a major portion, i.e., greater than 50 percent, of the cellulose fibers is preferably composed of normally dimensioned cellulose pulp, having a Canadian Standard Freeness of +400 to +800 ml. (hereinafter "normal cellulose pulp"). These fibers are typically relatively large, with commercially available diameters in the range of about 10 to about 60 microns and fiber lengths of from about 0.85 to about 6.5 mm. The minor portion, i.e., less than 50 percent, of the cellulose fibers, is refined pulp, exhibiting a Canadian Standard Freeness of +100 to −1000 ml. Such blends of normal cellulose pulp and refined cellulose pulp advantageously yield filter sheets in which the retention of particulate filter aid and particulate ion exchange resin is improved as compared to filter sheets prepared from normal cellulose pulp only. In a highly preferred embodiment of the present invention, a special grade of cellulose pulp is employed which possesses greater purity and greater carboxyl functionality compared to conventional grades of cellulose pulp. Such special grades are available commercially under the tradename MAC Sulphite, AA Sulphite and Alpha Hardwood Sulphite (Weyerhaeuser). The use of MAC Sulphite pulp is preferred in the practice of the present invention. Typical characteristics of a highly purified cellulose pulp which can be advantageously employed in the practice of the present invention are as follows:

| Property | Range | Preferred Range |
| --- | --- | --- |
| Brightness %[1] | 90–95 | 93–95 |
| Dirt (mm$^2$/m$^2$)[2] | 0.5–3 | 0.5–1 |
| Iron extractables (mg/kg) | 1–14 | 1–3 |
| Calcium extractables (mg/kg) | 50–300 | 50–100 |
| Copper extractables (mg/kg) | 0.1–5.0 | 0.1–0.5 |
| Manganese extractables (mg/kg) | 0.1–0.5 | 0.1–0.2 |

[1]TAPPI
[2]TAPPI

High purity cellulose pulps possess alpha-cellulose contents ranging from about 90 to about 95 percent and can be produced by the well-known and preferred sulphite process. Cellulose pulps possessing alpha-cellulose contents of greater than about 90 percent and high carboxyl functionality are preferred in the practice of the present invention.

The state of refinement of a cellulose fiber is determined by means of a "freeness" test in which measurement of the flow rate through a forming pad of the cellulose fiber on a standard screen is determined. Two of the most common instruments for the measurement of freeness are the "Canadian Standard Freeness Tester" and the "Schopper-Riegler Freeness Tester". In both of these methods, the quantity which is measured is the volume of water (expressed in ml) which overflows from a receiver containing an orifice outlet at the bottom. The Canadian Standard Freeness measurements are employed in the present specification. Coarse, unbeaten cellulose pulp, i.e., normal cellulose pulp, produces high drainage rates into the receiver from the screen resulting in large overflow volumes, and hence yields high freeness. Normal cellulose pulp exhibits Canadian Standard Freeness values ranging from +400 ml to +800 ml. Such pulp may be subjected to mechanical refining processes, i.e., beating, which cuts and/or fibrillates the cellulose fibers. Such refined fibers exhibit slower drainage rates, and, therefore, lower freeness values, i.e., in the range of +100 to −1000 ml. As refining is continued, the quantity of freeness in the overflow increases as more and more of the material passes through the screen. The freeness in this range is described as "inverted" and, for convenience, is accorded a negative value. By use of special refining equipment and long refining time, it is possible to achieve inverted Canadian Standard Freeness values of up to −1000 ml. There are several types of pulp refiners commercially available and these fall into two basic categories, namely, conical or jordan types, and disc types. The disc types, especially double-disc refiners, appear to be particularly suitable for the preparation of refined pulps.

Normal cellulose fibers can represent about 15 to about 80 weight percent of the filter sheet, with from about 15 to about 40 weight percent being preferred, from about 25 to about 40 weight percent being more preferred and from about 30 to about 40 weight percent being most preferred, to provide a filter sheet structural characteristics suitable for photoresist filtration applications. Refined cellulose pulp can represent from about 0 to about 45 weight percent of the filter sheet of this invention, with from about 5 to about 40 weight percent being preferred, from about 10 to about 30 weight percent being more preferred and from about 20 to about 30 weight percent being most preferred.

The use of refined pulp surprisingly results in a significant improvement in ion exchange capacity and a concomittant improvement in retention of particulates. Generally, the weight ratio of normal to refined pulp utilized in the practice of the present invention will range from about 1:1 to about 10:1, preferably from about 1.2:1 to about 3:1.

Performance is enhanced by maximizing the amount of particulate filter aid in the filter sheet of the invention. While as little as about 5 percent of a particulate filter aid will result in noticeable improvement in filtration performance, optimum performance is achieved by utilizing the maximum amount of particulate filter aid consistent with the aforementioned requirements for certain amounts of normal and refined wood pulp. For filtration of photoresist compositions, structural characteristics suggest employing a practicable maximum of about 40 percent by weight particulate filter aid. Of course, for less demanding applications, somewhat higher levels will be possible. Generally, levels of from about 15 to about 40 percent by weight particulate filter aid are employed, with levels of from about 20 preferred and levels eight percent being preferred and levels of from about 25 to about 35 weight percent being more preferred. In accordance with a preferred embodiment, the particulate filter aid is acid washed to remove metal impurities on the surfaces thereof. The acid can be any of hydrochloric acid, formic acid, acetic acid, propronic acid, butyric acid, oxalic acid, succinic acid, sulfonic acid, nitric acid, and the like. For example, particulate filter aid can be soaked in an HCl solution at pH of about 2 for 5–6 hours to remove metal impurities.

There are various types of particulate filter aids that can be advantageously employed in the practice of the present invention including diatomaceous earth, magnesia, perlite, talc, colloidal silica, polymeric particulates such as those produced by emulsion or suspension polymerization, e.g., polystyrene, polyacrylates, poly(vinyl acetate), polyethylene, (or other such materials as described in Emulsions and Emulsion Technology, Lissant, Kenneth J., Marcel Dekker, 1974), activated carbon, molecular sieves, clay, and the like. Functionally, the particulate filter aids employed in the practice of the present invention should have a specific surface area in excess of about 1.0 $m^2/g$ and/or particle diameters of less than about 15 microns, preferably less than about 10 microns, more preferably less than about 5 microns. In a broad sense, any conventional particulate filter aid can be employed (such as J.N. Filter Cel, Standard Super Cel, Celite 512, Hydro Super Cel, Speed Plus and Speedflow, Dicalite 215 and Dicalite 416 and Dicalite 436). From the standpoint of size, morphology, cost, fluid compatibility and general performance characteristics, the finer grades of diatomaceous earth and perlite particulate filter aids exhibiting a mean particle size of less than about 10 microns are preferred. Mixtures of more than one type of particulate filter aid can be employed where desired, e.g., to provide better filtration performance and/or better cost/performance characteristics than that achieved by the use of any single type by itself. Similarly, mixtures of relatively coarse and fine particulate filter aids may be utilized in the practice of the present invention.

Figure 1:
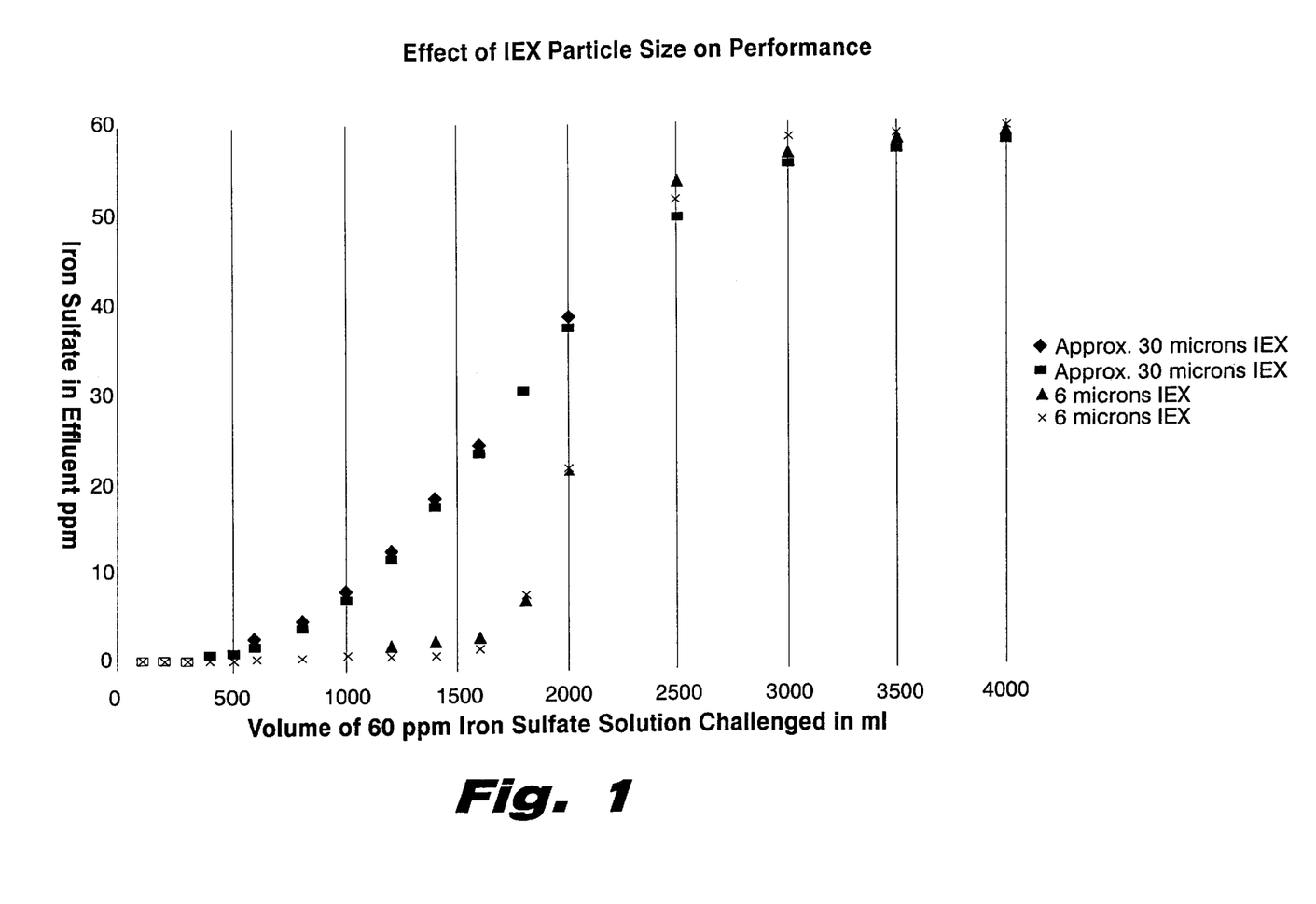
FIG. 1 graphically depicts the effect of ion exchange resin (IEX) particle size on the performance of the filter sheet of the present invention.

Particulate ion exchange resins which can be utilized in accordance with the present invention include cation exchange resins, anion exchange resins, and mixtures thereof. The ion exchange resins can be microreticular or macroreticular. The microreticular ion exchange resins are preferred. Ion exchange resin can represent from about 5 to about 65 weight percent, preferably from about 5 to about 35 weight percent, more preferably for about 5 to about 20 weight percent and most preferably from about 5 to about 15 weight percent, of the filter sheet of this invention. The average particle size of the ion exchange resin particles can broadly range from about 2 to about 200 microns. Smaller particle sizes can be obtained by grinding larger particles down to the desired size. The use of smaller particles improves the ion exchange efficiency of the filter sheet since smaller resin particles provide greater surface area. The use of smaller particles also results in the formation of filter sheets possessing a more restricted porosity. As a result of tighter porosity, the ion exchange resin particles come in close contact with each other, thereby increasing the efficiency of ion exchange between the resin and the organic liquid being purified. Ion exchange resin particles having an average particle size of from about 2 to about 10 microns have been found to yield particularly good results. FIG. 1 depicts a comparison of filter sheets produced using ion exchange resin particles having an average particle diameter of about 33 microns and filter sheets produced using ion exchange resin particles having an average particle diameter of about 6 microns. The relative amounts of ion exchange resin, cellulose pulp, diatomaceous earth and binder resin in each filter sheet were the same. The data presented in FIG. 1 demonstrates that use of smaller diameter ion exchange resin particles improves the exchange efficiency of the filter sheet.

Cation exchange resins which may be employed in the practice of the present invention are not particularly limited. Cation exchange resins which are capable of removing dissolved metal cations from photoresist compositions and are compatible with the photoresist, solvent, and other components of the photoresist composition can be advantageously employed in the practice of the present invention. Suitable cation exchange resins include sulfonated phenol-formaldehyde condensates, sulfonated phenol-benzaldehyde condensates, sulfonated styrene-divinyl benzene copolymers, sulfonated methacrylic acid-divinyl benzene copolymers, and other types of sulfonic or carboxylic acid group-containing polymers. It should be noted that cation exchange resins are typically supplied with $H^+$ counter ions, $NH_4^+$ counter ions or alkali metal, e.g., $K^+$ and $Na^+$ counter ions. Preferably, the cation exchange resin utilized herein will possess hydrogen counter ions. One preferred particulate cation exchange resin is Microlite PrCH available from Purolite (Bala Cynwyd, Pa.). This is a sulfonated styrene-divinyl benzene copolymer having a $H^+$ counter ion.

To remove dissolved anions from photoresist compositions, such as halides, phosphates, nitrates, chromates, borates, or other materials that can function as dopants in integrated circuits, the filter sheet of this invention can contain a particulate anion exchange resin. Suitable anion exchange resins are known in the art and are disclosed, for example, in Samuelson, *Ion Exchange Separations In Analytical Chemistry*, John Wiley & Sons, New York, 1963, Ch. 2, also incorporated herein by reference. The preferred anion exchange resins are those resins having a hydroxide counter ion whereby hydroxide is introduced into the photoresist composition during the exchange process. Hence, preferred anion exchange resins are those resins having quaternary ammonium hydroxide exchange groups chemically bound thereto, e.g., styrene-divinyl benzene copolymers substituted with tetramethylammoniumhydroxide. A preferred anion exchange resin is crosslinked polystyrene substituted with quaternary ammonium hydroxide such as the ion exchange resins sold under the trade names AMBERLYST® A-26-OH by Rohm and Haas Company and DOW G51-OH by Dow Chemical Company.

In accordance with a further embodiment of the invention, the filter sheet comprises a combination of a cation exchange resin having $H^+$ counter ions and an anion exchange resin having $OH^-$ counter ions. Utilizing this combination, during the photoresist purification process, water in minute amounts is introduced into the photoresist composition.

In accordance with another embodiment of the invention, in addition to ion exchange resin, the filter sheet can contain a chelating exchange resin for removing heavy metal ions. Typical chelating exchange resins are polyamines on polystyrene, polyacrylic acid and polyethyleneimine backbones, thiourea on polystryene backbones, guanidine on polystryene backbones, dithiocarbamate on a polyethyleneimine backbone, hydroxamic acid on a polyacrylate backbone, mercapto on polystyrene backbones, and cyclic polyamines on polyaddition and polycondensation resins. Chelating exchange resins can be employed in amounts which range from about 5 to about 65 weight percent, preferably from about 5 to about 15 weight percent, of the filter sheet of the invention.

The ion and chelating exchange resins are typically provided with alkali metal counter ions. Preferably, the alkali metal counter ions are removed from the resins prior to their use to prevent alkali metals from entering organic liquids which are passed through the filter sheet of the invention. This is accomplished by rinsing the resins with an acid. Though mineral acids may be used, weaker organic acids are also suitable. Accordingly, the acid can be any of hydrochloric acid, formic acid, acetic acid, propionic acid, butyric acid, oxalic acid, succinic acid, sulfuric acid, nitric acid, and the like. The treated resins can be dehydrated by washing the resins with an aqueous miscible organic solvent such as ethyl lactate, acetone or a solvent common to the organic liquid to be purified. This procedure can be performed at room or elevated temperature.

To fabricate the filter sheet of the present invention, a slurry of fibers, particulate filter aid and particulate ion exchange resin is formed. The sequence of adding these components to water to form the initial slurry appears to be relatively unimportant. The consistency of the slurry will represent the highest possible for a practical suspension of the components, usually less than about 4 percent, preferably less than about 3 percent, solids. The system is subjected to hydrodynamic shear forces utilizing well known techniques, e.g., a bladed mixer. Any suitable shear rate or shear stress may be employed to break up any flocs and maintain the system in a dispersed condition. Of course, upon the formation of a disperse slurry, the system is free of floc formation even in the absence of applied shear. To control the dispersion characteristics of negatively charged self-bonding fibers such as cellulose fibers and/or negatively charged particulate filter aid and to improve wet strength, binder resins are advantageously employed in the formation of the filter sheet of this invention. Such binder resins may be organic or inorganic polymers. Binder resins improve particulate retention and improve the strength of the filter sheet of this invention while in the wet or dry state. One or more of the fibers, particulate filter aid and particulate ion exchange resin can be pretreated with a binder resin prior to formation of the slurry or, preferably, the binder resin can be added to the slurry to facilitate the dispersion of self-bonding fibers and/or particulate filter aid in the slurry.

The slurry is diluted with additional water if necessary to the proper consistency required for vacuum felting sheet formation, ordinarily 1 to 2½ percent solids, depending upon the type of equipment used to form the sheet, in a manner known in the art. The slurry is cast onto a sheet and air dried in a standard manner. The method of drying is not critical, although faster drying sequences are preferred, hence elevated temperatures up to the decomposition or scorch point for the system are employed.

The specific choice of binder resin depends upon many factors, including cost, fluid and temperature compatibility, toxicology and supplementary functional attributes, such as cross-linking characteristics with cellulose and siliceous surfaces, in addition to the primary filtration performance factors. Selection of suitable binder resins from the broad categories specified above may be easily accomplished by methods well-known in the art. Melamine formaldehyde colloids such as those disclosed in U.S. Pat. Nos. 4,007,113 and 4,007,114, incorporated herein by reference, polyamido-polyamine epichlorhydrin resins such as those disclosed in U.S. Pat. No. 4,859,340, incorporated herein by reference, polyalkylene oxides such as those disclosed in U.S. Pat. No. 4,596,660, incorporated herein by reference, can be employed as binder resins in the practice of the present invention. Polyamido-polyamine epichlorhydrin resins are preferred in the practice of the present invention and can be obtained commercially, such as Polycup 1884, 2002 or S2063 (Hercules), Cascamide Resin pR-420 (Borden) and Nopcobond 35 (Nopco).

In accordance with a preferred embodiment of the present invention, the binder resins are employed in an amount sufficient to at least provide a disperse slurry, i.e., a slurry in which no visible flocculation occurs at ambient conditions in the absence of applied hydrodynamic shear forces. The slurry therefore comprises a uniform distribution of fibers, particulate filter aid and particulate ion exchange resin homogeneously distributed throughout the aqueous medium. The amount of binder resin necessary to form a uniform dispersion of fibers, particulate filter aid and particulate ion exchange resin can be readily determined by one skilled in the art. For example, polyamido-polyamine epichlorhydrin resin can be advantageously employed herein in amounts ranging from about 0.05 to about 2.0 weight percent, preferably from about 0.1 to about 0.5 weight percent, of the filter sheet.

The process of the invention is applicable to many organic liquids containing dissolved contaminants but is especially useful for treating photoresist compositions containing dissolved metal contaminants in ionic form. Accordingly, the description that follows will for the most part exemplify purification procedures for photoresist compositions, but the invention should not be construed as limited to this embodiment.

Photoresists are well known and described in numerous publications including DeForest, Photoresist Materials and Processes, McGraw-Hill Book Company, New York, Chapter 2, 1975 and Moreau, Semiconductor Lithography, Principles, Practices and Materials, Plenum Press, New York, Chapters 2 and 4, 1988, incorporated herein by reference.

Suitable positive-working photoresists typically contain two components, i.e., a light-sensitive compound and a film-forming polymer. The light-sensitive compound undergoes photochemical alteration upon exposure to radiation. Single component systems which employ polymers that undergo chain scission upon exposure to radiation are known. Light-sensitive compounds typically employed in two-component photoresist systems are esters formed from o-quinone diazide sulfonic acids, especially sulfonic acid esters of naphthoquinone diazides. These esters are well known in the art and are described in DeForest, supra, pages 47–55, and in Moreau, supra, pages 34–52. Light-sensitive compounds and methods used to make such compounds are disclosed in U.S. Pat. Nos. 3,046,110, 3,046,112, 3,046,119, 3,046,121, 3,106,465, 4,596,763 and 4,588,670, all incorporated herein by reference.

Polymers most frequently employed in combination with positive-working photoresists, e.g., o-quinone diazides, are the alkali soluble phenol formaldehyde resins known as the novolak resins. Photoresist compositions containing such polymers are described in U.S. Pat. Nos. 4,377,631 and 4,404,272. As disclosed in U.S. Pat. No. 3,869,292, another class of polymers utilized in combination with light-sensitive compounds are homopolymers and copolymers of vinyl phenol. The process of the instant invention is especially useful for the purification of positive-working photoresist compositions, such as the vinyl phenol-containing photoresist compositions.

Negative-working resist compositions can also be purified in accordance with the invention and are well known in the art. Such photoresist compositions typically undergo random crosslinking upon exposure to radiation thereby forming areas of differential solubility. Such rephotoinitiator. Oise a polymer and a photoinitiator. One class of negative-working photoresists comprises, for example, polyvinyl cinnamates as disclosed by R. F. Kelly, Proc. Second Kodak Semin. Micro Miniaturization, Kodak Publication P-89, 1966, p. 31. Other negative-working photoresists include polyvinyl-cinnamate acetates as disclosed in U.S. Pat. No. 2,716,102, azide cyclized rubber as disclosed in U.S. Pat. No. 2,940,853, polymethylmethacrylate/tetraacrylate as disclosed in U.S. Pat. No. 3,149,975, polyimide-methyl methacrylate as disclosed in U.S. Pat. No. 4,180,404 and polyvinyl phenol azide as disclosed in U.S. Pat. No. 4,148,655.

Another class of photoresists for purposes of the invention are those positive and negative acid-hardening resists disclosed in EP Application No. 0 232 972. These photoresists comprise an acid-hardening polymer and a halogenated, organic, photoacid generating compound.

Solvents for photoresists include, but are not limited to, alcohols, e.g., methanol, ethanol, isopropanol, etc.; esters, e.g., acetone, ethyl acetate, ethyl lactate, etc.; cyclic ethers, e.g., tetrahydrofuran, dioxane, etc.; ketones, e.g., acetone, methyl ethyl ketone, etc.; alkylene glycol ethers or esters, e.g., ethylene glycol ethyl ether, ethylene glycol ethyl ether acetate, ethylene glycol dimethyl ether, diethylene glycol dimethyl ether, propylene glycol monomethyl ether acetate, etc.; and the like. Other components typically found in photoresist compositions include colorants, dyes, adhesion promoters, speed enhancers, and surfactants such as non-ionic surfactants.

Essentially every component of a photoresist composition is a potential source of dissolved metallic contaminants that can deleteriously affect performance of an integrated circuit. Typical dissolved metal contaminants include sodium, potassium, iron, copper, chromium, nickel, molybdenum, zinc and mixtures of one or more thereof. Such metal impurities may also be in the form of colloidal particles such as insoluble colloidal iron hydroxides and oxides. In accordance with the process of the present invention, a photoresist solution comprising dissolved metal impurities typically in a polar organic solvent is passed through the filter sheet of this invention under suitable pressure to reduce the concentration of dissolved metal impurities to low parts per billion levels, e.g., to below about 100 ppb, preferably below about 75 ppb, more preferably below about 50 ppb and most preferably below about 35 ppb. The dissolved metal impurities can be initially present in the photoresist composition in individual concentrations of up to about 1,000 parts per million, typically up to about 500 parts per billion and more typically up to about 250 parts per billion. These concentrations are reduced by at least about 90 percent by weight, preferably by at least about 95 percent by weight, more preferably by at least about 99 percent by weight, in the practice of the present invention. The term "sheet filter" is utilized herein in its broadest sense and includes filtration elements in their original, substantially planar configuration and filtration elements fabricated from the original substantially planar configuration. For example, the term "sheet filter" encompasses leaf, tubular, pleated, flat membrane and spiral wound membrane filters. The pressure of the process stream passing through the filter sheet can broadly range up to about 50 psi, preferably up to about 35 psi. The flow rate of organic liquid through the filter sheet can broadly range up to about 1.2 gallons per minute (gpm) per square foot, preferably up to about 0.6 gpm per square foot.

Figure 2:
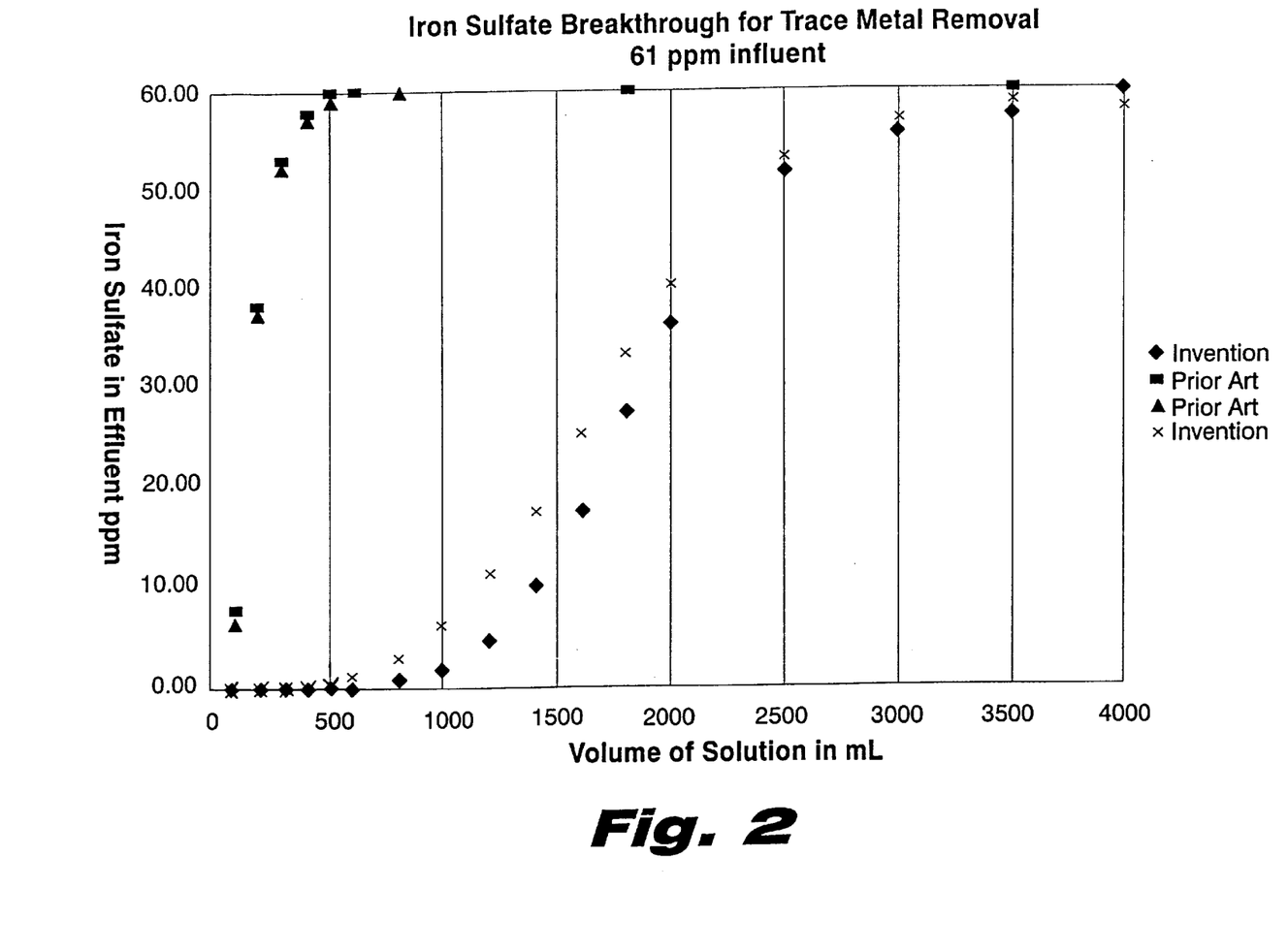
FIG. 2 is a graphical comparison of the performance of prior art filter sheets containing no ion exchange resin and the filter sheets of the instant invention.

FIG. 2 graphically depicts a comparison of the iron binding capacity of prior art filter sheets containing no ion exchange resin (sold under the tradename Zeta Plus® by Cuno Incorporated) and the filter sheets of the present invention (comprising 34.1 weight % cellulose pulp, 24.5 weight % refined cellulose pulp, 30.3 weight % acid washed diatomaceous earth, 11.5 weight % sulfonated styrene-divinyl benzene copolymer and 0.5 weight percent polyamido-polyamine epichlorhydrin resin). The data graphically depicted in FIG. 2 demonstrate that the filter sheet of the invention possesses approximately 10 times the iron binding capacity of the prior art filter sheet.

The following examples are illustrative of the present invention.

EXAMPLES 1–7

The ion exchange capacity of the individual components of the preferred filter sheet of the invention, i.e., ion exchange resin (sulfonated styrene-divinyl benzene copolymer sold under the tradename PrCH by Microlite, a division of Purolite Company, Bala Cynwyd, Pa.), normal cellulose pulp (MAC Sulfite pulp (Weyerhaeuser)), highly refined cellulose pulp (MAC Sulfite pulp (Weyerhaeuser)) and acid washed (AW) diatomaceous earth (DE) (Dicalite 215 (Grefco)), was measured with zinc sulfate in solution to determine the total potential capacity of each component[1]. Zinc sulfate is soluble over a wide pH range, will readily bind to the ion exchange resin, is easily detected and non-toxic. Other metal ions and other solvents would be expected to yield similar results.

The ion exchange capacity of each component was measured in a static soak test with zinc sulfate to determine the total potential capacity of each ingredient. The test results are summarized in Table 1 and show that only the ion exchange resin provides significant binding of the zinc ion.

TABLE 1

Static Soak Capacity of Filter Sheet Components in Water

| Constituent | Zinc Capacity (mg zinc/g constituent) |
|---|---|
| Ion Exchange Resin | 154 |
| Cellulose Pulp | <1 |
| Highly Refined Cellulose Pulp | <1 |
| Acid Washed DE 215 | <1 |

[1]The same components were utilized in all of the Examples.

Filter sheets containing varying levels of components were fabricated in the manner described hereinabove to determine the relative contribution of each component under flowing conditions. The relative amounts were standardized to make sheet to sheet comparison easier. The sheets were cut into 47 mm diameter discs for zinc sulfate solution challenge. Each sheet was challenged with 2000 ml of 38 ppm aqueous solution of zinc sulfate at 0.5 gpm/ft$^2$ and zinc removal was measured. In addition to measuring the total zinc removal, the zinc concentration in the effluent at 10 sample points during the test was measured to verify that the filter sheets had undergone complete breakthrough.

TABLE 2

Summary of Filter Sheet Properties and Results

| Example | 1 | 2 | 3 | 4 | 5 | 6 | 7 |
|---|---|---|---|---|---|---|---|
| Cellulose Pulp | 90% | 65% | 65% | 65% | 65% | 40% | 35% |
| Refined pulp | | 25% | 25% | | | 25% | 30% |
| AW DE 215 | | | | 25% | 25% | 25% | 25% |
| Exchange resin | 10% | 10% | 10% | 10% | 10% | 10% | 10% |
| PAE binder resin* | | | 0.5% | | 0.5% | 0.5% | 0.5% |
| AFAP in. H$_2$O | 0.9 | 6.6 | 6.9 | 0.9 | 1.1 | 16.5 | 24 |
| Pad Weight g | 25.6 | 23.7 | 24.1 | 20.8 | 22.4 | 24.1 | 23.8 |
| Average Cap mg/g | 8.6 | 11.3 | 12.6 | 10.9 | 9.4 | 13.1 | 13.9 |
| % Efficiency | 56 | 73 | 82 | 71 | 62 | 85 | 90 |

*Kymene 557H (Hercules).

Since only the ion exchange resin provided binding capacity and there is only 0.1 gram of ion exchange resin for every gram of filter sheet media for Examples 1–7, the maximum anticipated capacity for Examples 1–7 was 15.4 mg/g based on the static soak result. Surprisingly, the data presented in Table 2 demonstrate that capacity is improved by the individual addition of the refined pulp and the acid washed diatomaceous earth notwithstanding the fact that refined pulp and acid washed diatomaceous earth exhibited virtually no binding capacity at all.

EXAMPLES 8–11

The ion exchange capacity of the individual components of the preferred filter sheet of the invention, i.e., ion exchange resin, normal cellulose pulp and diatomaceous earth, was measured in a static soak test with zinc chloride in methanol under vigorous mixing to determine the total potential capacity of each component in a photoresist solvent. The zinc capacity was checked at 16 and 24 hours to verify that each component had reached equilibrium. The test results are summarized in Table 3 and show that only the ion exchange resin provides significant binding of the zinc ion in methanol. Compared to water, however, the ion exchange resin exhibited significantly lower activity in methanol, i.e., 73.4 mg. zinc/g. In water, the static soak capacity was 154 mg/g. (Table 1, supra).

TABLE 3

Static Soak Capacity of Filter Sheet Components in Methanol

| Constituent | Zinc capacity with vigorous mixing (mg. zinc/g component) |
|---|---|
| Ion Exchange Resin | 73.4 |
| Cellulose Pulp | 1.6 |
| Acid Washed DE 215 | 0.5 |

Filter sheets containing varying levels of components were fabricated to determine the relative contribution of each component under flowing conditions. (Example 8 is identical in formulation to Example 1, Example 9 is identical in formulation to Example 5, Example 10 is nearly identical in formulation to Example 3 and Example 11 is identical in formulation to Example 7). The amounts were standardized to make sheet to sheet comparison easier. The sheets were cut into 47 mm discs for zinc chloride solution challenge. Each sheet was challenged with 2000 ml of approximately 30 ppm aqueous solution of zinc chloride in methanol at 0.5 gpm/ft$^2$ and zinc removal was measured.

TABLE 4

Summary of Filter Sheet Properties and Results

| Example | 8 | 9 | 10 | 11 |
|---|---|---|---|---|
| Cellulose Pulp | 90% | 65% | 60% | 35% |
| Refined pulp | | | 30% | 30% |
| AWDE 215 | | 25% | | 25% |
| Ion Exchange resin | 10% | 10% | 10% | 10% |
| PAE resin | 0.5% | 0.5% | 0.5% | 0.5% |
| AFAP in. H$_2$O | 0.9 | 1.1 | 9.4 | 23.6 |
| Pad Weight g | 25.7 | 22.3 | 24.5 | 23.6 |
| Avg. capacity mg/g pad | 6.17 | 8.85 | 11.47 | 12.32 |

As shown in Table 4, the average dynamic capacity of the filter sheets surprisingly improved as the filter aid and refined pulp were added despite the fact that the static soak data suggested that they would offer little to no improvement. The data as a group clearly show that capacity was improved by the individual addition of the refined pulp and the acid washed diatomaceous earth.

The maximum theoretical capacity of the filter sheets were calculated for both water and methanol using the static soak results presented in Tables 1 and 3.

TABLE 5

Comparison of Dynamic and Static Results for Methanol and Water

| Dynamic Capacity Methanol mg/g | 6.17 (Example 8) | 8.85 (Example 9) | 11.47 (Example 10) | 12.32 (Example 11) |
|---|---|---|---|---|
| Dynamic Capacity Water mg/g | 8.60 (Example 1) | 9.40 (Example 5) | 12.6 (Example 3) | 13.9 (Example 7) |
| Maximum Theoretical Capacity (Methanol) | 8.78 (Example 8) | 8.51 (Example 9) | 8.78 (Example 10) | 8.51 (Example 11) |
| Maximum Theoretical Capacity (Water) | 15.4 (Example 1) | 15.4 (Example 5) | 15.4 (Example 3) | 15.4 (Example 7) |
| % Dynamic Methanol/Static Methanol | 70% | 104% | 131% | 145% |
| % Dynamic Methanol/Static Water | 40% | 57% | 74% | 80% |
| % Dynamic Methanol/Dynamic Water | 72% | 94% | 91% | 89% |

The data presented in Table 5 surprisingly and unexpectedly demonstrate that the dynamic capacity of those filter sheets which incorporated refined pulp and/or filter aid substantially exceeded the maximum static capacity calculated for those filter sheets in methanol. Moreover, the observed dynamic capacity of the filter sheets in methanol closely approached the observed dynamic capacity of the filter sheets in water. This result is particularly surprising in light of the static soak data which suggested that the ion exchange capacity of the filter sheets would significantly decrease in methanol as compared to water.

EXAMPLES 12–15

The metal extractables of the filter sheet of the invention was measured in ethyl lactate and propylene glycol monomethyl ether acetate (PGMEA) and the resulting data are summarized in Tables 7 and 8 below:

TABLE 7

| | Ethyl Lactate | | |
|---|---|---|---|
| Metal | LOQ[1] ppb | Example 12 (ppb) | Example 13 (ppb) |
| Sodium | 5.0 | <5.0 | 8.8 |
| Iron | 5.0 | <5.0 | <5.0 |
| Calcium | 1.0 | <1.0 | 3.6 |
| Chromium | 2.0 | <2.0 | <2.0 |
| Aluminum | 7.0 | <7.0 | <7.0 |
| Potassium | 1.0 | <1.0 | 1.2 |
| Copper | 1.0 | <1.0 | <1.0 |

[1]LOQ = Limit of Quantification

TABLE 8

| | PGMEA | | |
|---|---|---|---|
| Metal | LOQ ppb | Example 14 (ppb) | Example 15 (ppb) |
| Sodium | 5.0 | <5.0 | <5.0 |
| Iron | 5.0 | <5.0 | <5.0 |

TABLE 8-continued

| | | PGMEA | |
|---|---|---|---|
| Metal | LOQ ppb | Example 14 (ppb) | Example 15 (ppb) |
| Calcium | 4.0 | <4.0 | <4.0 |
| Chromium | 2.0 | <2.0 | <2.0 |
| Potassium | 1.0 | <1.0 | <1.0 |
| Copper | 1.0 | <1.0 | <1.0 |

Examples 12–15 were identically in formulation and comprised 34.1 weight % cellulose pulp, 24.5 weight % refined cellulose pulp, 30.3 weight % acid washed diatomaceous earth, 11.5 weight % weight sulfonated styrene-divinyl benzene copolymer and 0.5 weight % polyamido-polyamine epichorhydrin resin. The results were generated by flushing 75 mL of ethyl lactate or PGMEA through a 47 mm diameter filter sheet as made (no prior flush). The metals were analyzed by Graphite Furnace Atomic Absorption Spectroscopy (GFAAS). It can readily be seen that the filter sheet of the invention contains extremely low extractables, i.e., down to low parts per billion levels, which renders the subject filter sheet particularly useful for the purification of photoresist compositions where the reduction of metal impurities down to low ppb levels is highly desired. Preferably, the filter sheet of the invention contains sodium, iron, calcium, chromium, aluminum, potassium and copper extractables not exceeding about 20 ppb, more preferably not exceeding about 15 ppb, and most preferably not exceeding about 10 ppb, for each metal when measured by flushing 75 ml of a solvent selected from the group consisting of ethyl lactate and propylene glycol monomethyl ether acetate through the filter sheet measuring about 47 mm.

Obviously, modifications and variations of the present invention are possible in light of the foregoing disclosure. It is therefore to be understood that changes can be made in particular embodiments of the invention described which are within the full intended scope of the invention as defined by the claims which follow.

What is claimed is:

1. A filter sheet for filtering a photoresist composition comprising a self-supporting fibrous matrix having immobilized therein acid-washed particulate filter aid and particulate ion exchange resin particles having an average particle size of from about 2 to about 10 microns, wherein said particulate filter aid and ion exchange resin particles are distributed substantially uniformly throughout a cross-section of said matrix.

2. The filter sheet of claim 1 wherein the ion exchange resin is a cation exchange resin.

3. The filter sheet of claim 2 wherein the cation exchange resin is selected from the group consisting of sulfonated phenol-fomaldehyde condensates, sulfonated phenol-benzaldehyde condensates, sulfonated styrene-divinyl benzene copolymers and sulfonated methacrylic acid-divinyl benzene copolymers.

4. The filter sheet of claim 2 wherein the cation exchange resin is a sulfonated styrene-divinyl benzene copolymer.

5. The filter sheet of claim 1 wherein the ion exchange resin is a mixture of cation exchange resin and anion exchange resin.

6. The filter sheet of claim 1 wherein the particulate filter aid is selected from the group consisting of diatomaceous earth, magnesia, perlite, talc, colloidal silica, polymeric particulates, activated carbon, molecular sieves, clay and mixtures thereof.

7. The filter sheet of claim 1 wherein the particulate filter aid is diatomaceous earth.

8. The filter sheet of claim 1 further comprising a binder resin.

9. The filter sheet of claim 8 wherein the binder resin is polyamido-polyamine epichlorhydrin resin.

10. The filter sheet of claim 8 wherein the filter sheet contains from about 0.05 to about 2.0 weight percent binder resin.

11. The filter sheer of claim 8 wherein the filter sheer contains from about 0.01 to about 0.5 weight percent binder resin.

12. The filter sheet of claim 1 further comprising chelating exchange resin.

13. The filter sheet of claim 1 containing sodium, iron, calcium, chromium, aluminum, potassium and copper extractables not exceeding about 20 ppb for each metal when measured by flushing 75 mL of a solvent selected from the group consisting of ethyl lactate and propylene glycol monomethyl ether acetate through the filter sheet measuring about 47 mm in diameter.

14. The filter sheet of claim 1 wherein the self-supporting fibrous matrix comprises fiber selected from the group consisting of polyacrylonitrile fiber, nylon fiber, rayon fiber, polyvinyl chloride fiber, cellulose fiber, and cellulose acetate fiber.

15. The filter sheet of claim 1 wherein the self-supporting fibrous matrix comprises cellulose fiber.

16. The filter sheet of claim 15 wherein the cellulose fiber possesses an alpha cellulose content of greater than about 90 percent.

17. The filter sheet of claim 15 wherein the cellulose fiber comprises a major amount of normal cellulose pulp possessing a Canadian Standard Freeness of +400 to +800 mL and a minor amount of highly refined pulp possessing a Canadian Standard Freeness of +100 to −1000 mL.

18. The filter sheet of claim 1 wherein the filter sheet contains from about 5 to about 65 weight percent ion exchange resin.

19. The filter sheet of claim 1 wherein the filter sheet contains from about 5 to about 35 weight ion exchange resin.

20. The filter sheet of claim 1 wherein the filter sheet contains from about 5 to about 40 weight percent particulate filter aid.

21. The filter sheet of claim 1 wherein the filter sheet contains from about 15 to about 40 weight percent particulate filter aid.

22. The filter sheet of claim 1 wherein the filter sheet contains from about 15 to about 80 weight percent fibrous matrix.

23. The filter sheet of claim 1 wherein the filter sheet contains from about 40 to about 70 weight percent fibrous matrix.

24. The filter sheet of claim 1 wherein the filter sheet contains from about 5 to about 65 weight percent ion exchange resin, from about 5 to about 40 weight percent particulate filter aid, and from about 15 to about 80 weight percent fibrous matrix.

25. The filter sheet of claim 1 wherein the filter sheet contains from about 5 to about 35 weight percent ion exchange resin, from about 15 to about 40 weight percent particulate filter aid, and from about 40 to about 70 wieght percent fibrous matrix.

26. A filter sheet for filtering a photoresist composition comprising an ion exchange resin and an acid washed particulate filter aid immobilized in a self-supporting matrix of cellulose fiber comprising a major amount of normal cellulose pulp possessing a Canadian Standard Freeness of +400 to +800 ml and a minor amount of highly refined pulp possessing a Canadian Standard Freeness of +100 to −1000 mL.

27. The filter sheet of claim 26 wherein the cellulose fiber possesses an alpha-cellulose content of greater than about 90 percent.

28. The filter sheet of claim 26 wherein the ion exchange resin is a cation exchange resin containing H+ counter ions.

29. The filter sheet of claim 26 wherein the acid-washed particulate filter aid is diatomaceous earth.

30. The filter sheet of claim 26 further comprising a binder resin.

31. A filter sheet for filtering a photoresist composition comprising sulfonated styrene-divinyl benzene copolymer, acid-washed diatomaceous earth and polyamide-polyamine epichlorhydrin resin embedded in a self-supporting matrix of cellous fiber comprised of a major amount of normal cellulose pulp possessing a Canadian Standard Freeness of +400 to +800 mL and a minor amount of highly refined pulp possessing a Canadian Standard Freeness of +100 to −1000 mL.

32. The filter sheet of claim 31 wherein the filter sheet contains from about 5 to about 65 weight percent of sulfonated styrene-divinyl benzene copolymer.

33. The filter sheet of claim 31 wherein the filter sheet contains from about 5 to about 40 weight percent of diatomaceous earth.

34. The filter sheet of claim 31 wherein the filter sheet contains from about 0.05 to about 2 weight percent of polyamido-polyamine epichlorhydrin.

35. The filter sheet of claim 31 wherein the filter sheet contains from about 20 to about 80 weight percent of cellulose fiber.

* * * * *